United States Patent [19]

Soubrier et al.

[11] Patent Number: 5,736,323
[45] Date of Patent: Apr. 7, 1998

[54] AGENTS AND PROCEDURES FOR THE STUDY OF THE GENETIC POLYMORPHISM OF THE ANGIOTENSIN I CONVERTING ENZYME

[75] Inventors: Florent Soubrier, Paris; Christine Hubert, Sevres; Pierre Corvol, Paris, all of France

[73] Assignee: Institut National de la Sante et de la Recherche Medicale, Paris, France

[21] Appl. No.: 157,171
[22] PCT Filed: Jun. 24, 1992
[86] PCT No.: PCT/FR92/00574
§ 371 Date: Jan. 24, 1994
§ 102(e) Date: Jan. 24, 1994
[87] PCT Pub. No.: WO93/00360
PCT Pub. Date: Jan. 7, 1993

[30] Foreign Application Priority Data

Jun. 27, 1992 [FR] France ................... 91 08020

[51] Int. Cl.$^6$ ............... C12Q 1/68; C12P 19/34; C07H 21/04; C07H 21/02
[52] U.S. Cl. ............... 435/6; 435/91.2; 536/23.1; 536/24.3; 536/24.33
[58] Field of Search ............... 435/6, 91.2; 536/28.1, 536/24.3, 24.33

[56] References Cited

FOREIGN PATENT DOCUMENTS

WO 90/03435  4/1990  WIPO.
WO 91/00354  1/1991  WIPO.

OTHER PUBLICATIONS

Batzer et al., "Structure and Variability of Recently Inserted Alu Family Members", *Nucleic Acids Research*, 18, 6793–6798 (1990).

Lanzillo, "Chemiluminescent Nucleic Acid Detection with Digoxigenin–Labeled Probes: A Model System With Probes for Angiotensin Converting Enzyme Which Detect Less Than One Attomole of Target NDA", *Analytical Biochemistry*, 194, 45–53 (1991).

Rigat et al., "An Insertion/Deletion Polymorphism in the Angiotensin I–Converting Enzyme Gene Accounting for Half the Variance of Serum Enzyme Levels", *Journal of Clinical Investigation*, 86, 1343–1348 (1990).

*Primary Examiner*—W. Gary Jones
*Assistant Examiner*—Dianne Rees
*Attorney, Agent, or Firm*—Merchant, Gould, Smith, Edell, Welter & Schmidt, P.A.

[57] ABSTRACT

The invention discloses a method for detecting polymorphism in the angiotensin converting enzyme by means of a chain amplification technique, the aim being to detect whether or not the sequence of nucleotides 1451–1738 of intron 16 is present in the human angiotensin converting enzyme gene.

25 Claims, 4 Drawing Sheets

INTRON 15
(FIN)
AATGGGGCCTGGGGGCAGTGCAGGCCCCAGAGAGACCAAGTGCAAAAGGA
GTACAGCTCATTGCCTCTCCTTCCTCCTGCAG/

EXON 16
TACAACAAGATCCTGTTGGATATGGAAACCACCTACAGCGTGGCCACTGT
GTGCCACCCGAATGGCAGCTGCCTGCAGCTCGAGCCAG/

INTRON 16
GTGAGAGCTCATGTGCAGGCTGAGTGAGAGGCGAGGGCTGGGACTGGCAT
1
GGGGCCCGGGGGTGCTGGGTGAGAGCACAGAGTTGGGCTCCCCTCGCTCT
51
TGGGGTCAGCGTGCCCAGGAAATGCCCTTTCTTGTTTTCCACGAGGGGGG
101
CTTCTCTGCCCACTGAGAGCCGGCACCTACTTCATACCATGCCCCGATCA
151
GCTGCCCCTCCCTCAGAACCGCCCTCTGCTTAAGGGTGTCCACTCTCTCC
201
TGTCCTCTCTGCATGCCGCCCCTCAGAGCAGCGGGATCTCAAAGTTATAT
251
TTCATGGGCTTGGACTCCAAATGGGGGGAACTCGGGGACACTAGCTCCCC
301
CCGGCCTCCTTTCGTGACCCTGCCCTTGACTTCCTCACCTTCTCTGTCTT
351
TCCTGAGCCCCTCTCCCAGCATGTGACTGATAAGGAAATTGAGTCACACA
401
GCCCCTGAAAGCGCCAGACTAGAACCTGAGCCTCTGATTCCTCTCACTTC
451
CCTCCCCTACCCTGCCACTTCCTACTGGATAGAAGTAGACAGCTCTTGAC
501
TGTCCTCTTTTCTCCCCACTGGCTGGTCCTTCTTAGCCCCAGCCCGTTTG
551
AAAGAGCTCACCCCCGACACAAGGACCCGCACACAGATACCTCCCAGCTC
601
CCTCTCAACCCACCCTTTCCAGGGTTGGAGAACTTGAGGCATAAACATTC
651
TTCCATGAGGAATCTCCACCCAGAAATGGGTCTTTCTGGCCCCCAGCCCA
701
GCTCCCACATTAGAACAATGACAAATAGAAGGGGAAATGGAAAATAAACA
751
GGAGAAACGGTTTTCCCAGGACAGGGTTTGGCCTACAAGTTGTGGATGTG
801
GGTACCCATGCCAAGTGTGAGGGGAGGCTGGCCGGGTGTGGTGGCTCATG
851
CTCTAATCCCAGCACTTTGGGAGGCCAAGGTGAGTAGATCACTTGAGGCC
901
GGGAGTTTGAGACCAGCCTGGCCAACATGGTGAAACCCCATCTGTACTAA
951
AAATACAAAAGTTAGCTGGGCGTGGTGGTAGATGCCTGTAGTCCCAGCTA
1001

FIG. 2B

```
         CTTGGGAGGCTGAGGCATGAGAATCGCTTGAGCCCAGCCAGGGCAATACA
1051
         GCAAGACCCCGTCTCTACAAATAAAATACAAAAAATTAGTTGGATGTGGT
1101
         GGTGCATGCCTGTAGTCCTAGCTGCTAGGGAGGCTGAGATGGAAGGATTG
1151
         CTTGAGCCTGGGAGGTCAAGGCTGCAGTGAGCCGAGATGGCGCCACTGCA
1201
         CTCCAGCCTGGGCAACAGAGTGAGACCCTGTCTCAGAAAGAAAAAAAAAA
1251
         AAAAAGGAGAGGAGAGAGACTCAAGCACGCCCCTCACAGGACTGCTGAGG
1301
         CCCTGCAGGTGTCTGCAGCATGTGCCCAGGCCGGGGACTCTGTAAGCCAC
1351
         TGCTGGAGACCACTCCCATCCTTTCTCCCATTTCTCTAGACCTGCTGCCT
1401
         ATACAGTCACTTTTTTTTTTTTTTTGAGACGGAGTCTCGCTCTGTCGCCC
1451
         AGGCTGGAGTGCAGTGGCGGGATCTCGGCTCACTGCAACGTCCGCCTCCC
1501
         GGGTTCACGCCATTCTCCTGCCTCAGCCTCCCAAGTAGCTGGGACCACAG
1551
         CGCCCGCCACTACGCCCGGCTAATTTTTTGTATTTTTAGTAGAGACGGGG
1601
         TTTCACCGTTTTAGCCGGGATGGTCTCGATCTCCTGACCTCGTGATCCGC
1651
         CCGCCTCGGCCTCCCAAAGTGCTGGGATTACAGGCGTGATACAGTCACTT
1701
         TTATGTGGTTTCGCCAATTTTATTCCAGCTCTGAAATTCTCTGAGCTCCC
1751
         CTTACAAGCAGAGGTGAGCTAAGGGCTGGAGCTCAAGCCATTCAACCCCC
1801
         TACCAG/
```

EXON 17    ATCTGACGAATGTGATGGCCACATCCCGGAAATATGAAGACCTGTTATGG

GCATGGGAGGGCTGGCGAGACAAGGCGGGGAGAGCCATCCTCCAGTTTTA

CCCGAAATACGTGGAACTCATCAACCAGGCTGCCCGGCTCAATG/

INTRON 17  GTGAGTCCCTGCTGCCAACATCACTGGCACTTGGGTCCCTTCATTTTCCT

CAAAGAGGTGCTGTGAAACCCCAAGCCTAGGAAAAGGTAGATCCCTGGAG

GAGGCAGGTAATGTGGTGTTCGGAGAGCCTGGCTGTGTCCCCTCTGTAG/

FIG. 2C

EXON 18
GCTATGTAGATGCAGGGGACTCGTGGAGGTCTATGTACGAGACACCATCC
CTGGAGCAAGACCTGGAGCGGCTCTTCCAGGAGCTGCAGCCACTCTACCT
CAACCTGCATGCCTACGTGCGCCGGGCCCTGCACCGTCACTACGGGCCC
AGCACATCAACCTGGAGGGGCCCATTCCTGCTCACCTGCTGG/

INTRON 18
(DEBUT)
GTAAGGGCACATGTCGGGCCTTGAGGAGGGTAAAGACGGACCACAGTGTG
AGTGAGGGTTGGGACAGGGCTGACTAGAGGGTAGGGAGCAGGCTGGGGAC
TGAGAGACTCCAGCCCTGTGGGGATGGTTGCCCAGGCT...

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear     ( i i ) MOLECULE TYPE: DNA (genomic)

( v i i ) IMMEDIATE SOURCE:
        ( B ) CLONE: Intron 15

( x i ) SEQUENCE DESCRIPTION: SEQ ID NO:1:

```
AATGGGGCCT  GGGGGCAGTG  CAGGCCCCAG  AGAGACCAAG  TGCAAAAGGA  GTACAGCTCA        60

TTGCCTCTCC  TTCCTCCTGC  AG                                                    82
```

( 2 ) INFORMATION FOR SEQ ID NO:2:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear     ( i i ) MOLECULE TYPE: DNA (genomic)

( v i i ) IMMEDIATE SOURCE:

( B ) CLONE: Exon 16

( x i ) SEQUENCE DESCRIPTION: SEQ ID NO:2:

```
TACAACAAGA  TCCTGTTGGA  TATGGAAACC  ACCTACAGCG  TGGCCACTGT  GTGCCACCCG      60
AATGGCAGCT  GCCTGCAGCT  CGAGCCAG                                            88
```

( 2 ) INFORMATION FOR SEQ ID NO:3:

( i ) SEQUENCE CHARACTERISTICS:
        ( A ) LENGTH: 1856 base pairs
        ( B ) TYPE: nucleic acid
        ( C ) STRANDEDNESS: single
        ( D ) TOPOLOGY: linear     ( i i ) MOLECULE TYPE: DNA (genomic)

( v i i ) IMMEDIATE SOURCE:
        ( B ) CLONE: Intron 16 of human angiotension converting
            enzyme (ACE) gene ( x i ) SEQUENCE DESCRIPTION: SEQ ID NO:3:

```
GTGAGAGCTC  ATGTGCAGGC  TGAGTGAGAG  GCGAGGGCTG  GGACTGGCAT  GGGGCCCGGG      60
GGTGCTGGGT  GAGAGCACAG  AGTTGGGCTC  CCCTCGCTCT  TGGGGTCAGC  GTGCCCAGGA     120
AATGCCCTTT  CTTGTTTTCC  ACGAGGGGGG  CTTCTCTGCC  CACTGAGAGC  CGGCACCTAC     180
TTCATACCAT  GCCCCGATCA  GCTGCCCCTC  CCTCAGAACC  GCCCTCTGCT  TAAGGGTGTC     240
CACTCTCTCC  TGTCCTCTCT  GCATGCCGCC  CCTCAGAGCA  GCGGGATCTC  AAAGTTATAT     300
TTCATGGGCT  TGGACTCCAA  ATGGGGGGAA  CTCGGGACA   CTAGCTCCCC  CCGGCCTCCT     360
TTCGTGACCC  TGCCCTTGAC  TTCCTCACCT  TCTCTGTCTT  TCCTGAGCCC  CTCTCCCAGC     420
ATGTGACTGA  TAAGGAAATT  GAGTCACACA  GCCCCTGAAA  GCGCCAGACT  AGAACCTGAG     480
CCTCTGATTC  CTCTCACTTC  CCTCCCTAC   CCTGCCACTT  CCTACTGGAT  AGAAGTAGAC     540
AGCTCTTGAC  TGTCCTCTTT  TCTCCCCACT  GGCTGGTCCT  TCTTAGCCCC  AGCCCGTTTG     600
AAAGAGCTCA  CCCCGACAC   AAGGACCCGC  ACACAGATAC  CTCCAGCTC   CCTCTCAACC     660
CACCCTTTCC  AGGGTTGGAG  AACTTGAGGC  ATAAACATTC  TTCCATGAGG  AATCTCCACC     720
CAGAAATGGG  TCTTTCTGGC  CCCAGCCCA   GCTCCCACAT  TAGAACAATG  ACAAATAGAA     780
GGGGAAATGG  AAAATAAACA  GGAGAAACGG  TTTTCCCAGG  ACAGGGTTTG  GCCTACAAGT     840
TGTGGATGTG  GGTACCCATG  CCAAGTGTGA  GGGGAGGCTG  GCCGGGTGTG  GTGGCTCATG     900
CTCTAATCCC  AGCACTTTGG  GAGGCCAAGG  TGAGTAGATC  ACTTGAGGCC  GGGAGTTTGA     960
GACCAGCCTG  GCCAACATGG  TGAAACCCCA  TCTGTACTAA  AAATACAAAA  GTTAGCTGGG    1020
CGTGGTGGTA  GATGCCTGTA  GTCCAGCTA   CTTGGGAGGC  TGAGGCATGA  GAATCGCTTG    1080
AGCCCAGCCA  GGGCAATACA  GCAAGACCCC  GTCTCTACAA  ATAAAATACA  AAAATTAGT    1140
TGGATGTGGT  GGTGCATGCC  TGTAGTCCTA  GCTGCTAGGG  AGGCTGAGAT  GGAAGGATTG    1200
CTTGAGCCTG  GGAGGTCAAG  GCTGCAGTGA  GCCGAGATGG  CGCCACTGCA  CTCCAGCCTG    1260
GGCAACAGAG  TGAGACCCTG  TCTCAGAAAG  AAAAAAAAA   AAAAAGGAGA  GGAGAGAGAC    1320
TCAAGCACGC  CCCTCACAGG  ACTGCTGAGG  CCCTGCAGGT  GTCTGCAGCA  TGTGCCCAGG    1380
CCGGGGACTC  TGTAAGCCAC  TGCTGGAGAC  CACTCCATC   CTTTCTCCCA  TTTCTCTAGA    1440
CCTGCTGCCT  ATACAGTCAC  TTTTTTTTT   TTTTGAGAC   GGAGTCTCGC  TCTGTCGCCC    1500
AGGCTGGAGT  GCAGTGGCGG  GATCTCGGCT  CACTGCAACG  TCCGCCTCCC  GGGTTCACGC    1560
CATTCTCCTG  CCTCAGCCTC  CCAAGTAGCT  GGGACCACAG  CGCCCGCCAC  TACGCCCGGC    1620
TAATTTTTTG  TATTTTTAGT  AGAGACGGGG  TTTCACCGTT  TTAGCCGGGA  TGGTCTCGAT    1680
```

| CTCCTGACCT | CGTGATCCGC | CCGCCTCGGC | CTCCCAAAGT | GCTGGGATTA | CAGGCGTGAT | 1740 |
| ACAGTCACTT | TTATGTGGTT | TCGCCAATTT | TATTCCAGCT | CTGAAATTCT | CTGAGCTCCC | 1800 |
| CTTACAAGCA | GAGGTGAGCT | AAGGGCTGGA | GCTCAAGCCA | TTCAACCCCC | TACCAG | 1856 |

( 2 ) INFORMATION FOR SEQ ID NO:4:

( i ) SEQUENCE CHARACTERISTICS:
        ( A ) LENGTH: 144 base pairs
        ( B ) TYPE: nucleic acid
        ( C ) STRANDEDNESS: single
        ( D ) TOPOLOGY: linear     ( i i ) MOLECULE TYPE: DNA (genomic)

( v i i ) IMMEDIATE SOURCE:
        ( B ) CLONE: Exon 17

( x i ) SEQUENCE DESCRIPTION: SEQ ID NO:4:

| ATCTGACGAA | TGTGATGGCC | ACATCCCGGA | AATATGAAGA | CCTGTTATGG | GCATGGGAGG | 60 |
| GCTGGCGAGA | CAAGGCGGGG | AGAGCCATCC | TCCAGTTTTA | CCCGAAATAC | GTGGAACTCA | 120 |
| TCAACCAGGC | TGCCCGGCTC | AATG | | | | 144 |

( 2 ) INFORMATION FOR SEQ ID NO:5:

( i ) SEQUENCE CHARACTERISTICS:
        ( A ) LENGTH: 149 base pairs
        ( B ) TYPE: nucleic acid
        ( C ) STRANDEDNESS: single
        ( D ) TOPOLOGY: linear     ( i i ) MOLECULE TYPE: DNA (genomic)

( v i i ) IMMEDIATE SOURCE:
        ( B ) CLONE: Intron 17

( x i ) SEQUENCE DESCRIPTION: SEQ ID NO:5:

| GTGAGTCCCT | GCTGCCAACA | TCACTGGCAC | TTGGGTCCCT | TCATTTCCT | CAAAGAGGTG | 60 |
| CTGTGAAACC | CCAAGCCTAG | GAAAAGGTAG | ATCCCTGGAG | GAGGCAGGTA | ATGTGGTGTT | 120 |
| CGGAGAGCCT | GGCTGTGTCC | CCTCTGTAG | | | | 149 |

( 2 ) INFORMATION FOR SEQ ID NO:6:

( i ) SEQUENCE CHARACTERISTICS:
        ( A ) LENGTH: 192 base pairs
        ( B ) TYPE: nucleic acid
        ( C ) STRANDEDNESS: single
        ( D ) TOPOLOGY: linear     ( i i ) MOLECULE TYPE: DNA (genomic)

( v i i ) IMMEDIATE SOURCE:
        ( B ) CLONE: Exon 18

( x i ) SEQUENCE DESCRIPTION: SEQ ID NO:6:

| GCTATGTAGA | TGCAGGGGAC | TCGTGGAGGT | CTATGTACGA | GACACCATCC | CTGGAGCAAG | 60 |
| ACCTGGAGCG | GCTCTTCCAG | GAGCTGCAGC | CACTCTACCT | CAACCTGCAT | GCCTACGTGC | 120 |
| GCCGGGCCCT | GCACCGTCAC | TACGGGCCC | AGCACATCAA | CCTGGAGGGG | CCCATTCCTG | 180 |
| CTCACCTGCT | GG | | | | | 192 |

( 2 ) INFORMATION FOR SEQ ID NO:7:

( i ) SEQUENCE CHARACTERISTICS:
        ( A ) LENGTH: 138 base pairs (B) TYPE: nucleic acid
(C) STRANDEDNESS: single
(D) TOPOLOGY: linear (ii) MOLECULE TYPE: DNA (genomic)

(vii) IMMEDIATE SOURCE:
(B) CLONE: Intron 18

(xi) SEQUENCE DESCRIPTION: SEQ ID NO:7:

| | | | | | |
|---|---|---|---|---|---|
| GTAAGGGCAC | ATGTCGGGCC | TTGAGGAGGG | TAAAGACGGA | CCACAGTGTG | AGTGAGGGTT  60 |
| GGGACAGGGC | TGACTAGAGG | GTAGGGAGCA | GGCTGGGGAC | TGAGAGACTC | CAGCCCTGTG  120 |
| GGGATGGTTG | CCCAGGCT | | | |  138 |

(2) INFORMATION FOR SEQ ID NO:8:

(i) SEQUENCE CHARACTERISTICS:
(A) LENGTH: 288 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

| | | | | | |
|---|---|---|---|---|---|
| ATACAGTCAC | TTTTTTTTT | TTTTGAGAC | GGAGTCTCGC | TCTGTCGCCC | AGGCTGGAGT  60 |
| GCAGTGGCGG | GATCTCGGCT | CACTGCAACG | TCCGCCTCCC | GGGTTCACGC | CATTCTCCTG  120 |
| CCTCAGCCTC | CCAAGTAGCT | GGGACCACAG | CGCCCGCCAC | TACGCCCGGC | TAATTTTTG  180 |
| TATTTTTAGT | AGAGACGGGG | TTTCACCGTT | TTAGCCGGGA | TGGTCTCGAT | CTCCTGACCT  240 |
| CGTGATCCGC | CCGCCTCGGC | CTCCCAAAGT | GCTGGGATTA | CAGGCGTG | 288 |

AGENTS AND PROCEDURES FOR THE STUDY OF THE GENETIC POLYMORPHISM OF THE ANGIOTENSIN I CONVERTING ENZYME

BACKGROUND OF THE INVENTION

The cloning of cDNAs corresponding to the gene coding for the human angiotensin converting enzyme (ACE) has made it possible to use it as a DNA probe for investigating DNA polymorphism in this gene in man.

The interest of this research in DNA polymorphisms was multiple. On the one hand, it was known that the plasma level of the ACE was stable and the effect of an allele on a major gene had been suggested following a familial study. It was thus logical to want to know whether the ACE gene itself was responsible for the effect of the major gene and to discover the importance of the interpersonal differences of the ACE level as a function of the genotype. On the other hand, it was of interest to have available a genetic marker which could be used to test the involvement of the gene in certain diseases, such as hypertension, by association or binding studies.

From the clinical point of view, the plasma level of the ACE was measured in 80 normal individuals and their genotypes were determined. Significant differences were observed between the ACE level of the individuals as a function of their ACE genotype (Rigat, B. et al. (1990), Journal of Clinical Investigation, 1343–1346).

The research into polymorphism was conducted by using the Southern blot method. The DNA of different individuals was digested by several restriction enzymes. After hybridization with the cDNA probe for ACE, it was apparent that some fragments did not have the same size in all individuals. The fact that the difference in size between the polymorphic fragments was apparently very similar with different enzymatic cleavages led to the conclusion that this polymorphism was due to the presence or absence of a DNA sequence (designated hereafter insertion) within the ACE gene.

SUMMARY OF THE INVENTION

The invention follows from the location of the insertion in intron 16 (SEQ ID NO:3) of the gene, i.e. between exon 16 (SEQ ID NO:2) and exon 17 (SEQ ID NO:4) after the nucleotide structure of this intron had itself been determined. The sequencing of the intron, and more particularly of the regions flanking the insertion and the insertion itself has enabled the inventors to determine the nature of the insertion. It is a repetitive sequence of the Alu type.

Hence, the subject of the invention is products, in particular nucleotide fragments deriving from this observation, more particularly primers which can be used in gene amplification procedure, for example amplification by PCR ("polymerase chain reaction") type.

BRIEF DESCRIPTION OF THE DRAWINGS

FIGS. 2 (a), 2 (b) and 2 (c) present the sequences of intron 16 and exons (exons 16 and 17 SEQ ID NO:2 and SEQ ID NO:4, respectively) which surround and flank intron 16 (SEQ ID NO:3) in the ACE gene. Only the nucleotides (nt) of intron 16 (SEQ ID:8) are numbered. FIG. 2a also includes intron 15 (SEQ ID NO:1). FIG. 2b also includes intron 17 (SEQ ID NO:5). FIG. 2c includes exon 18 (SEQ ID NO:6) and intron 18 (SEQ ID NO:7).

The sequence which is present or absent depending on the individual comprises the nucleotides 1451 to 1738 (SEQ ID NO:8).

DESCRIPTION OF THE PREFERRED EMBODIMENTS

Figure 1:
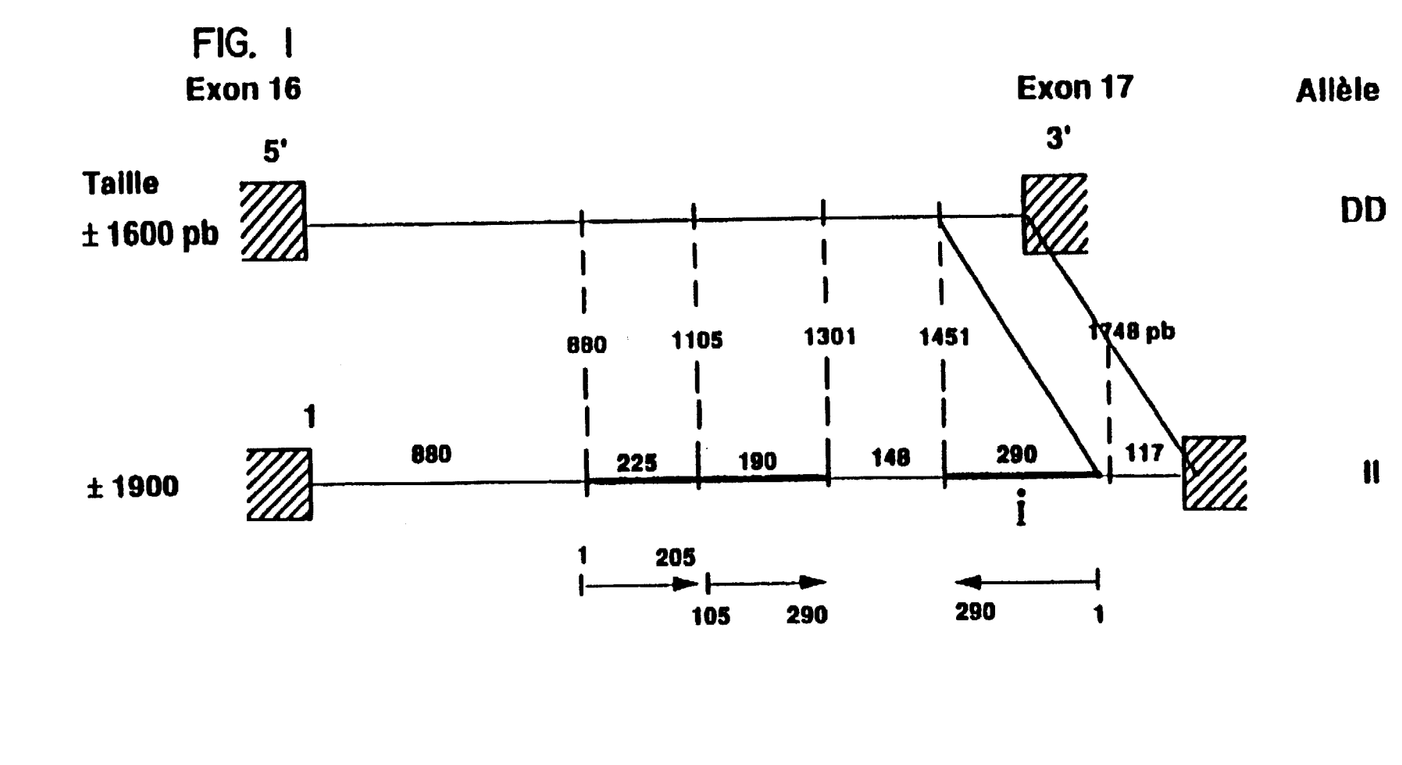
FIG. 1 shows to the general organization of intron 16 in alleles derived from subjects who possess the insertion (II) and from those who lack it (DD), respectively.
Figure 2A:
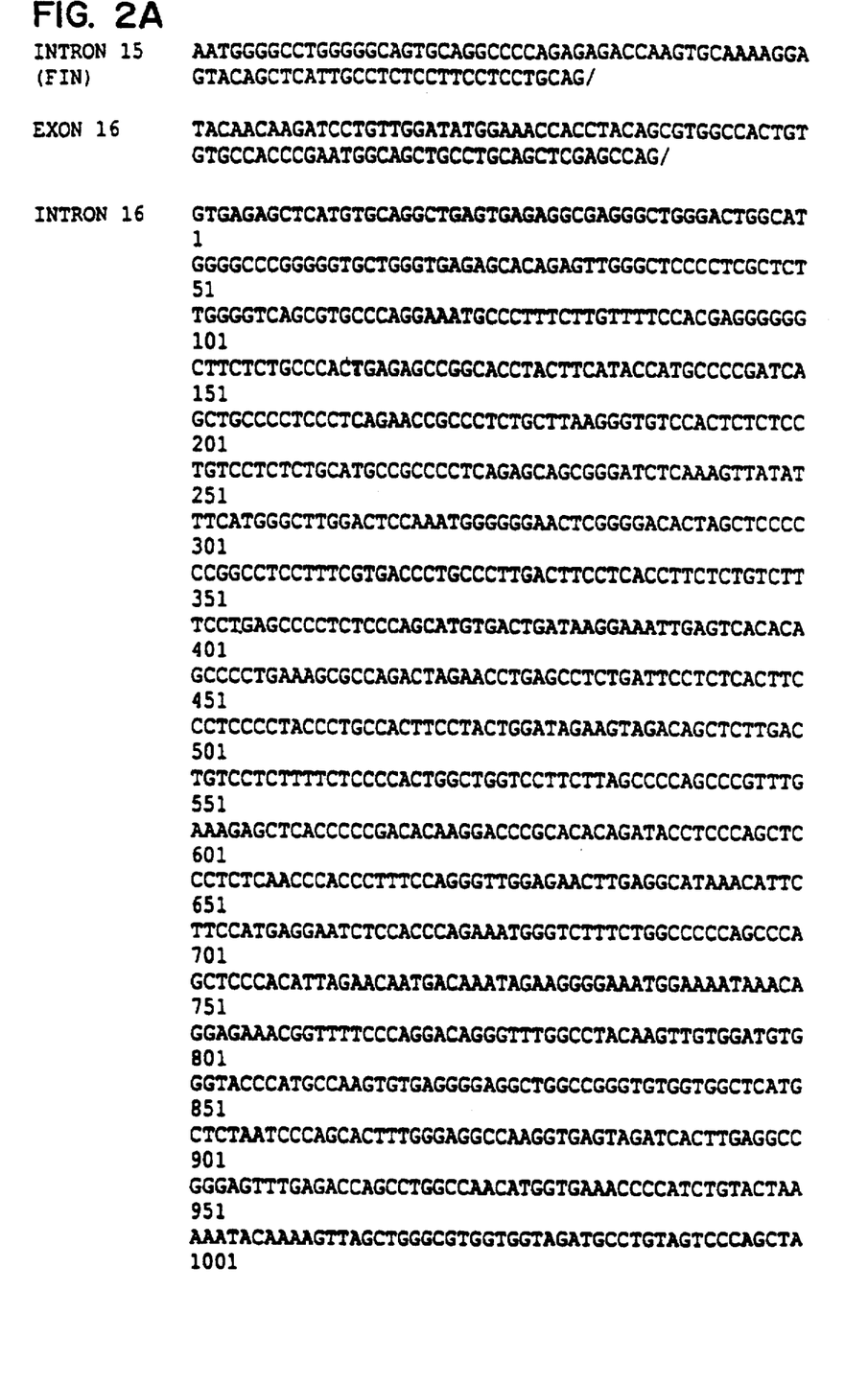
Figure 2B:
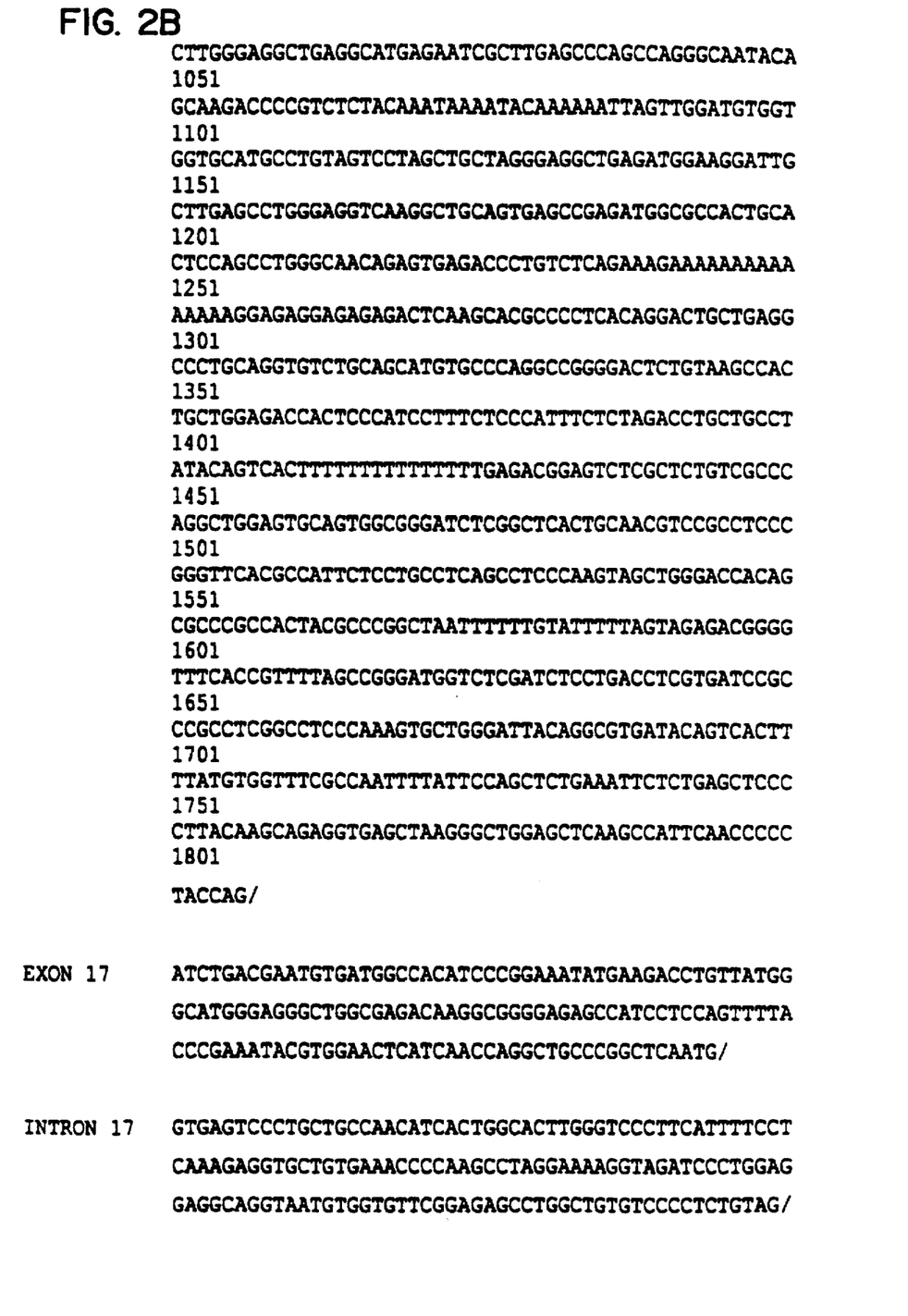
Figure 2C:
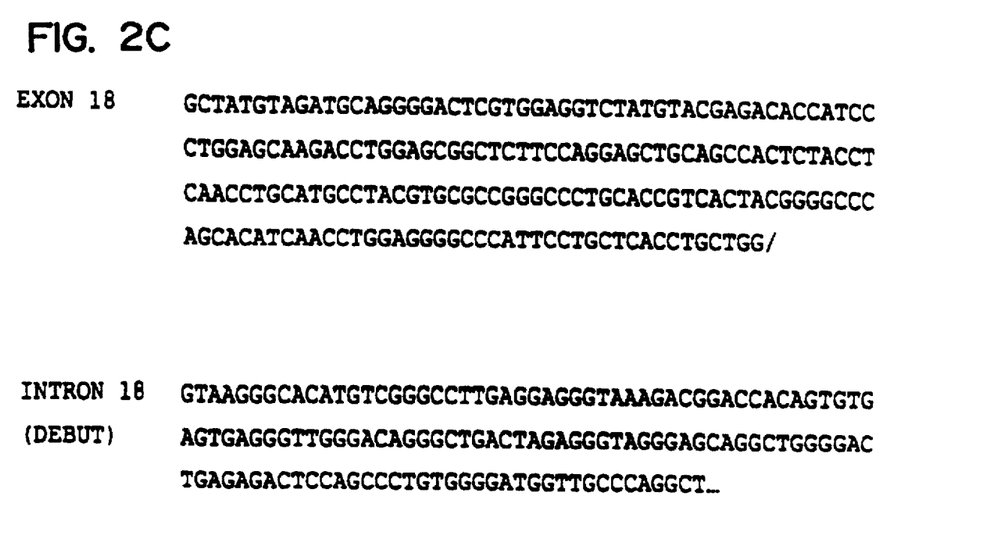

The invention relates more particularly to any DNA fragment comprising at least 8 nucleotides and characterized by a sequence contained in the DNA of intron 16 (nt 1–1856 shown in FIG. 1) (SEQ ID NO:3) and, consequently, having a maximum of 1856 nucleotides. However, it relates more particularly to any one of the following fragments.

DNA fragment, characterized in that it contains all or part of the sequence nt. 1451–1738 (SEQ ID NO:8) (insertion);

DNA fragment, characterized in that it is placed entirely within the insertion.

DNA fragment, characterized in that it contains at least one of the regions flanking the above-mentioned insertion.

DNA fragment, characterized in that its sequence lies outside the insertion sequence nt. 1451–1738 (SEQ ID NO:8).

Advantageously, these various DNA fragments comprise from 15 to 40 nucleotides.

The invention relates more particularly to pairs of distinct fragments selected from those previously mentioned, which can be used to design primers which can be used in sequence amplification procedures, in particular of the PCR type, these distinct fragments comprising non-overlapping sequences of nucleotides.

These primer pairs are, for example:

characterized in that their intrinsic sequences are such that the intermediate sequence placed in the DNA of the intron between the two sequences which, within the same intron, correspond to those of these two primers, overlaps at least one of the ends (nt.1451 or 1738) of the insertion (nt. 1451–1738) (SEQ ID NO 18) and the flanking region which is adjacent to it.

characterized in that the sequence of one of the two primers overlaps one of the ends (nt.1451 or 1738) of the insertion or lies outside the latter and in that the sequence of the other primer overlaps the other end (nt.1738 or 1451) of the insertion or also lies outside the latter.

characterized in that the sequence of one of the two primers overlaps one of the ends (nt.1451 or 1738) of the insertion or lies outside the latter and in that the sequence of the other primer is included in the insertion.

Hence the invention relates more particularly to the procedure for the detection of polymorphism within the gene for the angiotensin I converting enzyme (ACE gene), characterized by the search for, in particular by hybridization or sequence amplification procedures, and the detection of the presence or absence of the insertion nt.1451–1738 (SEQ ID NO:8) within intron 16 (SEQ ID NO:3) of the ACE gene. For example, a procedure of the PCR type is used by employing one of the primer pairs defined hereafter and an attempt is made to detect amplified chains likely to comprise both at least one of the terminal parts of the insertion and at least one of the two flanking regions.

A positive result then reveals the presence of the insertion, whereas a negative result signals the absence of such an insertion.

It will be obvious that the specialist skilled in the art may then have recourse to any standard procedure to have access to the genomic DNA of the cells obtained from the subject (in particular from his blood serum) whose polymorphism is to be studied.

The procedure according to the invention may, for example, be implemented as follows. It comprises:

a) the placing of the biological sample under study containing the ACE gene, in particular intron 16 (SEQ ID NO:3), made accessible beforehand to a first primer under conditions allowing the hybridization between this primer and the DNA of the gene, in the presence of nucleoside triphosphates and an agent inducing polymerization (polymerase), wherein the polymerization starts from these primers hybridized to the cDNA of the gene in order to produce—where appropriate—a duplex formed between the elongation product of the primer hybridized with the intron, b) the denaturation of the duplex obtained at step a) so as to "separate" the elongation product of the primer from the DNA to be detected, c) the placing of the elongation product obtained in contact with the second primer which has a nucleotide sequence (1) which is not complementary to a sequence of the elongation product previously formed, d) where necessary, the repetition of the steps a), b) and c) in the presence of the first and second primers used in excess and reagents necessary for the production of further elongation products used in turn as matrices for additional syntheses until a sufficient quantity is obtained for the elongation products of the primers used to be detected.

e) the detection (where necessary) of the presence of the elongation products characteristic of the presence of at least a part of the insertion (nt.1451–1738) (SEQ ID NO:8).

For more details concerning the method relating to the detection procedure described above or for the development of variants of this procedure, it will be useful for the person skilled in the art to refer to the principles described in the patents U.S. Pat. No. 4,683,202 and U.S. Pat. No. 4,683,195.

As a result of using two primers located on either side of at least a part of the polymorphic region, it is possible to easily visualize the difference in size due to the presence or absence of the insertion, for example by migration of the amplified fragments on agarose gel and staining with ethidium bromide, wherein the possibility to determine the genotypes of the individuals under study by means of the amplification reaction of the DNA.

Consequently, the invention provides a procedure for the determination of polymorphism affecting normal and abnormal ACE values, in particular for the study of its impact on diseases (for example, in diabetic individuals suffering from a sarcoidosis) which, according to observations already made, were accompanied by an increase in ACE plasma levels.

Similarly, the results likely to be obtained by the implementation of the procedure according to the invention ought to make possible a better understanding of the degree to which ACE polymorphism is implicated in the metabolism of vasoactive peptides and in the mechanisms of hypertension.

The procedure according to the invention can be used with particular advantage to the in vitro diagnosis of atherosclerosis, granulomatous diseases and complications in diabetes mellitus,

---

We claim:

1. A DNA fragment consisting of at least about 8 to about 1856 consecutive nucleotides of a sequence of intron 16 (SEQ. ID NO:3) of a human angiotensin converting enzyme gene.

2. The DNA fragment according to claim 1, wherein the fragment consists of all or part of nucleotides 1451–1738 of intron 16 (SEQ. ID NO:8) of a human angiotensin converting enzyme gene.

3. The DNA fragment according to claim 2, wherein the sequence of the fragment consists of a subsequence of SEQ. ID NO:8.

4. A DNA fragment wherein the fragment consists of at least 8 contiguous nucleotides from nucleotides 1451–1738 of intron 16 (SEQ. ID NO:3) of a human angiotensin converting enzyme gene and at least one of the sequences flanking nucleotides 1451–1738 of intron 16 (SEQ. ID NO:3) of a human angiotensin converting enzyme gene, wherein the flanking sequences consist of sequences from intron 16, exon 16, or exon 17 of a human angiotensin converting enzyme gene.

5. The DNA fragment according to claim 1, wherein the sequence in the DNA of intron 16 includes nucleotides 1–1450 or 1739–1856 of intron 16 (SEQ ID NO:3) of a human angiotensin converting enzyme gene.

6. The DNA fragment according to claim 1, wherein the fragment consists of about 15 to about 40 nucleotides.

7. A pair of DNA fragments according to claim 1, wherein the fragments are primers used in a sequence amplification.

8. The primers according to claim 7, wherein the sequence is amplified using a polymerase chain reaction.

9. The primers according to claim 7, wherein the pair of DNA fragments comprise a first primer and a second primer, which primer pair is selected from the group consisting of:

a primer pair in which the first primer consists of a subsequence of nucleotides 1–1450 of intron 16 (SEQ. ID NO:3); and a primer pair in which the first primer consists of a subsequence of nucleotides 1–1737 of intron 16 (SEQ. ID NO:3) and the second primer consists of a subsequence of nucleotides 1739–1856 of intron 16 (SEQ. ID NO:3).

10. The primers according to claim 7, wherein the pair of DNA fragments comprise a first primer and a second primer, which primer pair is selected from the group consisting of:

a primer pair in which the first primer is a subsequence of intron 16 and comprise nucleotide 1451 of intron 16 (SEQ. ID NO:3) and the second primer is a subsequence of intron 16 and comprises nucleotide 1738 of intron 16 (SEQ. ID NO:3); and a primer pair in which the sequence of the first primer and the sequence of the second primer each consist of from 15 to 40 consecutive nucleotides outside of nucleotides 1451–1738 of intron 16 (SEQ. ID NO:3).

11. The primers according to claim 7, wherein the pair of DNA fragments comprise a first primer and a second primer which primer pair is selected from the group consisting of:

a primer pair in which the first primer is a subsequence of intron 16 and comprises nucleotide 1451 of intron 16 (SEQ. ID NO:3) and the second primer consists of a subsequence of nucleotides 1451–1738 of intron 16 (SEQ. ID NO:3);

a primer pair in which the first primer is a subsequence of intron 16 and comprises nucleotide 1738 of intron 16 (SEQ. ID NO:3) and the second primer consists of a subsequence of nucleotides 1451–1738 of intron 16 (SEQ. ID NO:3); and a primer pair in which the first primer consists of a sequence of from 15 to 40 nucleotides that lies outside of nucleotides 1451–1738 of intron 16 (SEQ. ID NO:3) and the second primer consists of a of nucleotides 1451–1738 of intron 16 (SEQ. ID NO:3).

12. A pair of DNA fragments used as primers for amplifying a sequence of intron 16 (SEQ. ID NO:3) of a human angiotensin converting enzyme gene.

13. The pair of DNA fragments used as primers according to claim 12, wherein a first primer consists a sequence selected from the group consisting of a subsequence of intron 15 (SEQ. ID NO:1), a subsequence of exon 16 (SEQ. ID NO:2), a subsequence of exon 17 (SEQ. ID NO:4), a subsequence of intron 17 (SEQ. ID NO:5), a subsequence of exon 18 (SEQ. ID NO:6), and a subsequence of intron 18 (SEQ. ID NO:7) and a second primer consists of a different sequence from said first primer and is selected from the group consisting of a subsequence of intron 15 (SEQ. ID NO:1), a subsequence of exon 16 (SEQ. ID NO:2), a subsequence of exon 17 (SEQ. ID NO:4), a subsequence of intron 17 (SEQ. ID NO:5), a subsequence of exon 18 (SEQ. ID NO:6), and a subsequence of intron 18 (SEQ. ID NO:7).

14. The pair of DNA fragments used as primers according to claim 12, wherein the pair of DNA fragments comprise a first primer and a second primer, wherein the first primer consists of a subsequence of nucleotides 1451–1738 of intron 16 (SEQ. ID NO:3) and the second primer comprises a sequence selected from the group consisting of a subsequence of intron 15 (SEQ. ID NO:1), a subsequence of exon 16 (SEQ. ID NO:2), a subsequence of exon 17 (SEQ. ID NO:4), a subsequence of intron 17 (SEQ. ID NO:5), a subsequence of exon 18 (SEQ. ID NO:6), and a subsequence of intron 18 (SEQ. ID NO:7).

15. A pair of DNA fragments according to claim 12, wherein the sequence is amplified using a polymerase chain reaction.

16. A method for the detection of a polymorphism within a gene for angiotensin converting enzyme in a biological sample, the method comprising the steps of:

hybridizing a pair of primers to a DNA sequence encoding a human angiotensin converting enzyme;

amplifying said DNA sequence; and detecting the presence or absence of all or part of nucleotides 1451–1738 (SEQ. ID NO:8) of intron 16 (SEQ. ID NO:3) of the human angiotensin converting enzyme gene.

17. The method according to claim 16, wherein the sequence is amplified using a polymerase chain reaction.

18. The method according to claim 16, wherein said sequence amplification step includes a pair of primers.

19. The method according to claim 18, wherein each primer of the pair of primers consists of at least about 8 to about 1856 consecutive nucleotides of a sequence in intron 16 (SEQ. ID NO:3) of a human angiotensin converting enzyme gene.

20. The method according to claim 19, wherein the pair of primers comprises a first primer and a second primer, which primer pair is selected from the group consisting of:

a primer pair in which the first primer consists of a subsequence of nucleotides 1–1450 of intron 16 (SEQ. ID NO:3) and the second primer consists of a subsequence of nucleotides 1452–1856 of intron 16 (SEQ. ID NO:3); and a primer pair in which he first primer consists of a subsequence of nucleotides 1–1737 of intron 16 (SEQ. ID NO:3) and the second primer consists of a subsequence of nucleotides 1739–1856 of intron 16 (SEQ. ID NO:3).

21. The method according to claim 19, wherein sequence amplification comprises a first primer and a second primer, which primer pair is selected from the group consisting of:

a primer pair in which the first primer is a subsequence of intron 16 and comprises nucleotide 1451 of intron 16 (SEQ. ID NO:3) and the second primer consists of a subsequence of intron 16 and comprises nucleotide 1738 of intron 16 (SEQ. ID NO:3);

a primer pair in which the first primer is a subsequence of intron 16 and comprises nucleotide 1738 of intron 16 (SEQ. ID NO:3) and the second primer is subsquence of intron 16 an comprises nucleotide 1451 of intron 16 (SEQ. ID NO:3); and a primer pair in which the sequence of the first primer and the sequence of the second primer each consist of sequences that lie outside of nucleotides 1451–1738 of intron 16 (SEQ. ID NO:3).

22. The method according to claim 19, wherein the pair of primers comprises a first primer and a second primer, which primer pair is selected from the group consisting of:

a primer pair in which the first primer is subsequence of intron 16 and comprises nucleotide 1451 of intron 16 (SEQ. ID NO:3) and the second primer consists of a subsequence of nucleotides 1451–1738 of intron 16 (SEQ. ID NO:3); and a primer pair in which the first primer is a subsequence of intron 16 and comprises nucleotide 1738 of intron 16 (SEQ. ID NO:3) and the second primer consists of a subsequence of nucleotides 1451–1738 of intron 16 (SEQ. ID NO:3); and a primer pair in which the first primer consists of a sequence that lies outside the range of nucleotides 1451–1738 of intron 16 (SEQ. ID NO:3) and the second primer consists of a subsequence of nucleotides 1451–1738 of intron 16 (SEQ. ID NO:3).

23. The method according to claim 18, wherein each of the pair of primers has a sequence selected from the group consisting of a subsequence of intron 15 (SEQ ID NO:1), a subsequence of exon 16 (SEQ ID NO:2), a subsequence of exon 17 (SEQ ID NO:4), a subsequence of intron 17 (SEQ ID NO:5), a subsequence of exon 18 (SEQ ID NO:6), and a subsequence of intron 18 (SEQ ID NO:7).

24. The method according to claim 18, wherein the pair of primers includes a first primer and a second primer, the first primer consisting of a subsequence of nucleotides 1451–1738 of intron 16 (SEQ. ID NO:3) and the second primer consists of a sequence selected from the group consisting of a subsequence of intron 15 (SEQ. ID NO:1), a subsequence of exon 16 (SEQ. ID NO:2), a subsequence of exon 17 (SEQ. ID NO:4); a subsequence of intron 17 (SEQ. ID NO:5), a subsequence of exon 18 (SEQ. ID NO:6), and a subsequence of intron 18 (SEQ. ID NO:7).

25. A DNA fragment comprising at least about 8 to 1856 consecutive nucleotides of a sequence of intron 16 SEQ. ID NO:3) of a human angiotensin converting enzyme gene.

* * * * *

UNITED STATES PATENT AND TRADEMARK OFFICE
CERTIFICATE OF CORRECTION

PATENT NO. : 5,736,323
DATED : APRIL 7, 1998
INVENTOR(S) : SOUBRIER ET AL.

It is certified that error appears in the above-identified patent and that said Letters Patent is hereby corrected as shown below:

Title page, [30] Foreign Data: "1992" should read —1991—

Col. 1, line 63: insert —(SEQ. ID No: 3)— after the numeral "16"

Col. 1, line 66: "(SEQ. ID:8)" should read —(SEQ. ID No: 3)—

Col. 2, line 38: "(SEQ. ID No 18)" should read —(SEQ. ID No: 8)—

Col. 10, line 47, claim 10: "comprise" should read —comprises—

Col. 11, line 4, claim 11: insert —subsequence— after the word "a"

Col. 12, line 17, claim 21: insert —a— after the word "is"

Col. 12, line 27, claim 22: insert —a— after the word "is"

Signed and Sealed this

Sixth Day of July, 1999

*Attest:*

Q. TODD DICKINSON

*Attesting Officer*   Acting Commissioner of Patents and Trademarks